United States Patent [19]
Bhatnagar et al.

[11] Patent Number: 5,817,680
[45] Date of Patent: Oct. 6, 1998

[54] HEMOREGULATORY COMPOUNDS

[75] Inventors: Pradip Kumar Bhatnagar, Exton; Dirk Heerding, Ardmore, both of Pa.

[73] Assignee: Smithkline Beecham Corportion, Philadelphia, Pa.

[21] Appl. No.: 522,225

[22] PCT Filed: Jul. 21, 1995

[86] PCT No.: PCT/US95/09158

§ 371 Date: Jan. 21, 1997

§ 102(e) Date: Jan. 21, 1997

[87] PCT Pub. No.: WO96/03398

PCT Pub. Date: Feb. 8, 1996

[51] Int. Cl.⁶ .......................... A61K 31/44; C07D 413/04
[52] U.S. Cl. .......................... 514/340; 546/271.4; 546/256
[58] Field of Search .......................... 546/271.4; 514/340

[56] References Cited

PUBLICATIONS

Brunner, et al., "Asymmetric catalysis. XLV. Enantioselective hydrosilyation of ketones with [Rh(COD)CL]2/pyridinyloxazoline catalysts", (1989), Chemical Abstracts, vol. 17, No. 17, abstract no. 154196, Chem. Ber. (1989), 122(3), 499–507.

Haidukewych, et al., "Mild conversion of carboxylic acids to 2–oxazolines and their utility as a crboxyl masking group against lithium aluminum hydride", (1972), Chemical Abstracts, vol. 77, No. 17, see abstract no. 114288, Tetrahedron Lett. (1972) (30), 3031–4.

*Primary Examiner*—Alan L. Rotman
*Attorney, Agent, or Firm*—Linda E. Hall; Stephen A. Venetianer

[57] ABSTRACT

The present invention relates to novel compounds which have hemoregulatory activities and can be used to inhibit the myelopoietic system of humans and animals.

4 Claims, No Drawings

HEMOREGULATORY COMPOUNDS

FIELD OF THE INVENTION

The present invention relates to novel compounds which have hemoregulatory activities and can be used to inhibit the myelopoietic system of humans and animals.

BACKGROUND OF THE INVENTION

A variety of regulatory messengers and modifiers such as colony stimulating factors, interferons, and different types of peptides are responsible for the regulation of myelopoiesis.

We have now found certain compounds which have an inhibitory effect on myelopoietic cells in vitro. They may be used to prevent quiescent cells from entering into cell division. Cells entering into cell division are susceptible to attack by cytotoxic anti-cancer drugs. In addition to providing a protective function in therapy using cytotoxic drugs, the compounds may also be used to arrest proliferation of cancer cells related to the myelopoietic system, i.e. myeloid leukemia.

SUMMARY OF THE INVENTION

This invention comprises compounds, hereinafter represented as formula (I), which have hemoregulatory activities and can be used to inhibit haematopoiesis.

The compounds are useful in providing a protective function in therapy using irradiation and/or cytotoxic drugs, and may also be used to arrest proliferation of cancer cells related to the myelopoietic system, for example, in the treatment of myeloid leukemia. The compounds may also be used in many clinical situations where it is desirable to alter haematopoiesis.

These compounds may also be used in combination with the dimers of co-pending U.S. application Ser. No.08/001,905, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity. This invention is also a pharmaceutical composition, which comprises a compound of formula (I) and a pharmaceutically acceptable carrier.

This invention further constitutes a method for inhibiting the myelopoietic system of an animal, including humans, which comprises administering to an animal in need thereof, an effective amount of a compound of formula (I).

DETAILED DESCRIPTION OF THE INVENTION

The compounds of this invention are illustrated by the Formula (I):

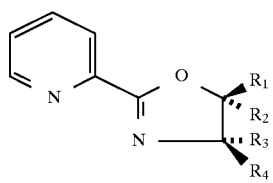

wherein $R_1$ and $R_2$ are independently hydrogen, $C_{1-6}$alkyl, phenyl, napthyl, benzyl, pyridyl, furyl, oxazolyl or thiazolyl;

$R_3$ and $R_4$ are independently hydrogen, —$CO_2H$, —$(CH_2)_nOH$, —$C(O)NH_2$, tetrazole, —$CO_2(C_{1-3}$alkyl), $C(O)C_{1-3}$alkyl, $CSNH_2$, $C_{1-6}$alkyl or —$(CH_2)_nCO_2H$; n is 1, 2 or 3;

provided at least one of $R_1$ and $R_2$ and one of $R_3$ and $R_4$ is not hydrogen;

or a pharmaceutically acceptable salt thereof.

Also included in this invention are pharmaceutically acceptable salt complexes of the compounds of this invention.

Preferred compounds are:

(4S,5R)-4,5-Dihydro-5-methyl-2-(2-pyridinyl)oxazole-4-carboxylic acid;

(4S,5S)-4,5-Dihydro-5-methyl-2-(2-pyridinyl)oxazole-4-carboxylic acid;

(4S,5R)-4,5-Dihydro-5-methyl-2-(2-pyridinyl)oxazole-4-carboxamide; and (4R,5R)-4,5-Dihydro-5-methyl-2-(2-pyridinyl)oxazole-4-carboxylic acid.

The present invention provides compounds of Formula (I) above

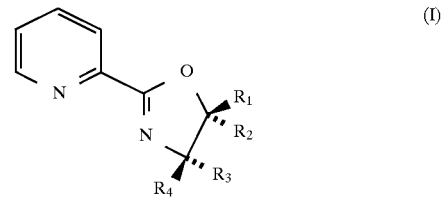

which can be prepared by a process that comprises:

a) reacting a compound of Formula (2)

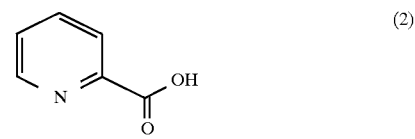

with a substituted amino-alcohol of Formula (3)

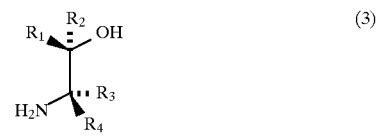

wherein $R_1$ and $R_2$ are independently selected from H, $C_{1-6}$alkyl, phenyl, napthyl, benzyl, pyridyl, furyl, oxazolyl or thiazolyl. $R_3$ and $R_4$ are independently selected from H, $CONH_2$, $CSNH_2$, $(CH_2)_nOH$, $(CH_2)_nCO_2H$, tetrazole, —$COO(C_{1-3}$alkyl), —$C(O)C_{1-3}$alkyl or $C_{1-6}$alkyl in a suitable solvent such as DMF with a coupling reagent such as N-Ethyl-N'(3-dimethylaminopropyl)carbodiimide hydrochloride (EDC) and a tertiary amine such as triethyl amine to provide a compound of Formula (4).

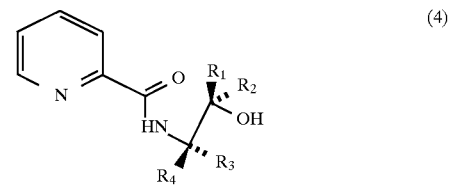

Cyclization of compound (4) in the presence of Burgess Reagent (methoxycarbonylsulfamoyl)-triethylammonium hydroxide, inner salt, in refluxing THF provides oxazolines of Formula (5).

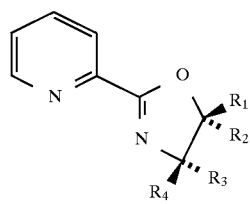

(5)

The treatment of compounds of Formula (5), wherein $R_3$ or $R_4$ is an ester, with a base such as sodium hydroxide in suitable solvent such as aqueous ethanol affords compounds of Formula (I).

The compounds of Formula (I) where either $R_3$ or $R_4$ is $CONH_2$ can be obtained by the aminolysis of compounds of Formula (5) wherein $R_3$ or $R_4$ is ester.

In general, in order to exert a inhibitory effect, the compounds of the invention may be administered to human patients by injection in the dose range of about 0.5 ng to about 10 mg, for example about 5–500 ng, or orally in the dose range of about 50 ng to about 5 mg, for example about 0.1 ng to 1 mg per 70 kg body weight per day; if administered by infusion or similar techniques, the dose may be in the range of about 0.005 ng to about 10 mg per 70 kg body weight, for example about 0.03 ng to 1 mg over six days. In principle, it is desirable to produce a concentration of the peptide of about $10^{-15}$M to about $10^{-5}$M in the extracellular fluid of the patient.

According to a still further feature of the present invention there are provided pharmaceutical compositions comprising as active ingredient one or more compound of formula (I) as hereinbefore defined or physiologically compatible salts thereof, in association with a pharmaceutical carrier or excipient. The compositions according to the invention may be presented; for example, in a form suitable for oral, nasal, parenteral or rectal administration.

As used herein, the term "pharmaceutical" includes veterinary applications of the invention. These compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueous suspension. Such a liquid formulation may be administered directly p.o. or filled into a soft gelatin capsule. Organ specific carrier systems may also be used.

Alternately pharmaceutical compositions of the compounds of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the compounds of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 1 mg–100 mg, for example 0.1–50 mg of the peptide of formula (I) or salt thereof.

According to a still further feature of the present invention there is provided a method of inhibition of myelopoiesis which comprises administering an effective amount of a pharmaceutical composition as hereinbefore defined to a subject.

No unacceptable toxicological effects are expected when compounds of the invention are administered in accordance with the present invention. The myelosuppressive activity of the compounds of Formula (1) was evaluated in either of the following assays:

Inhibition of Murine HPP-CFC (High Proliferative Potential Colony Forming Cells) Colony Formation The $Lin^-Sca1^+$(HPP-CFC) cells are isolated from femurs and tibia of normal female C57BL/6J mice. Single cell suspension is obtained by crushing the femurs and tibia then filtering the suspension through a 70 micron filter. Cells are washed and incubated in PBS+1% FBS (fetal bovine serum) at a concentration of $10^8$ cells/ml with an optimal concentration of a cocktail of monoclonal antibodies directed against various lineage markers. After 30 minutes on ice, the cells are washed and the Lin marker expressing cells are removed with magnetic beads coated with the sheep anti rat IgG. Cells are washed in PBS+1% FBS buffer and resuspended to a concentration of $10^8$ cells/ml. Optimal concentration of Ly6A/E-FITC (from Pharmingen) is added to the suspension and the cells are incubated for 30–45 minutes. The cells positive for Ly6A/E and negative for anti rat IgG are analyzed and sorted in a Coulter Epics Elite Cell Sorter equipped with a 488 nM tuned argon ion laser set to give a power of 15 mW with a rate of 1500–2000 cells/second (Coulter Electronics CA, USA). The final recovery of cells is 0.05–0.1% of the unfractionated bone marrow. The Lin-Sca1+ cells are seeded in a double layer semisolid agar colony forming assay.

The compounds of Formula (I) are dissolved in PBS+1% FBS to give concentrations ranging from 1 mg/ml to 0.1 ng/ml. Four hundred Lin-Sca1+ cells are seeded in the presence or absence of the compound. The cells are stimulated with a cocktail of Il-1, Il-3 and SCF (stem cell factor). The HPP colonies are defined as colonies larger than 0.5 mm diameter The difference between the colony number observed with the PBS buffer and the target compound solution is the measure of inhibition the compounds of the invention. The compounds of the invention gave activities ranging from 0.1 ng/ml to 10 mg/ml.

SK&F 107647 Antagonism Assay

This assay monitors the capacity of compounds of Formula (I) to inhibit the myelo-stimulatory activity of SK&F 107647:

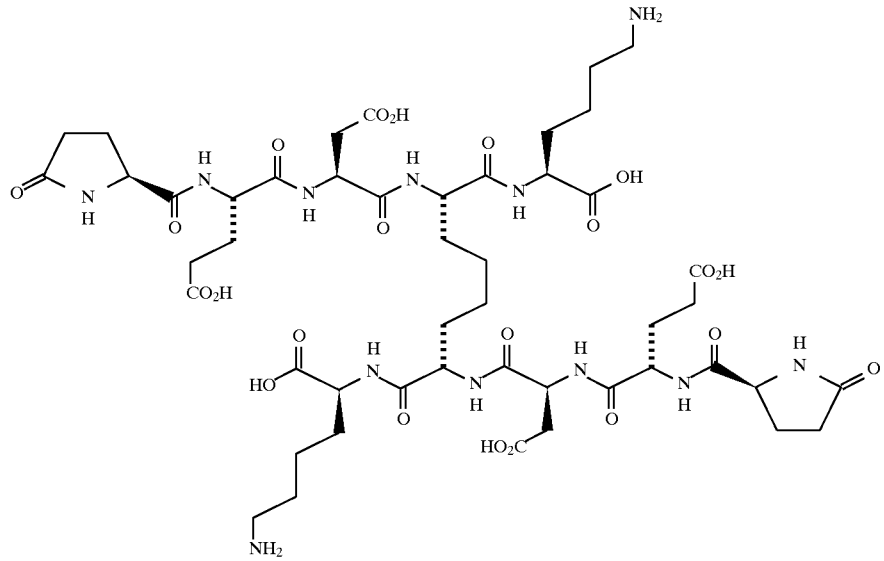

The murine bone marrow derived stromal cell line, C6.4 are grown in 12 well plates in RPMI 1640 with 10% FBS. Upon reaching confluence, C6.4 cells are washed and media exchanged with fresh RPMI 1640 without FBS. Confluent cell layers of murine C6.4 cells are treated with SK&F 107647 (1 microgram/ml) which results in the production of a soluble hematopoietic synergistic activity measurable in a murine CFU-C assay (described below). The compounds of Formula (I) alone do not induce synergistic activity production from the stromal cell line. The compounds of Formula (I) are added to C6.4 cell cultures immediately prior to the addition of SK&F 107647. Cell-free supernatants are collected 18 hours later. Supernatants are fractionated with a Centricon-30 molecular weight cut-off membrane. C6.4 cell synergistic activity is measured in a murine CFU-C assay.

CFU-C Assay (Colony Forming Unit in Culture Assay)

Bone marrow cells from C57B 1/6 female mice are cultured in nutrient rich media with 0.3% agar and a source of colony stimulating factor (CSF) for a period of 6–7 days at 37° C. in a humidified atmosher of 7.5% $CO_2$. Cell aggregates >50 cells are counted as collonies (CFU-c).

The Combination of SK&F 107647 treated C6.4 cell 30 K-effluent (30 K-E) with sub optimal levels of CSF results in colony growth greater than CSF alone. Murine bone marrow cells are harvested then suspended in RPMI 1640 with 10% FBS. Bone marrow cells (7.5E+4 cells/ml) are cultured with sub optimal levels of CSF plus dilutions of test C6.4 cell 30 K-E supernatants in a standard murine soft agar CFU-C assay. The SK&F 107647 treated culture 30 K-E represents the stimulated activity level. The combination of compounds of Formula I with SK&F 107647 can result in several different outcomes:

1) synergistic activity equal to SK&F 107647=not active as antagonist
2) synergistic activity significantly less that SK&F 107647=weak antagonist
3) no synergistic activity=antagonist or toxicity (requires separate test in CFU-C assay)

Data analysis: by convention 1 Unit (U) is equal to 1 colony stimulated* above background CSF alone CFU-C number.

[* statistically significant by t test].

Example:

CSF=20 CFU-C colonies

CSF+0.05 ml 30 K-E=50 CFU-C colonies

Calculated activity=30 Units/0.05 ml or 600 U/ml

The compounds of the invention showed activity at concentrations ranging from 10 ng/ml to 1 mg/ml.

The examples which follow serve to illustrate this invention. The Examples are intended to in no way limit the scope of this invention, but are provided to show how to make and use the compounds of this invention.

In the examples, all temperatures are in degrees Centigrade.

EXAMPLE 1

(4S, 5R)-4,5-Dihydro-5-methyl-2-(2-pyridinyl) oxazole4-carboxylic acid

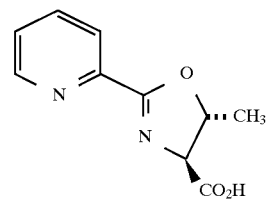

a) N-Picolinyl-allo-threonyl methyl ester (Pic-allo-ThrOMe)

To a suspension of allo-ThrOMeoHCl (3.50 g, 20.4 mmol) in $CHCl_3$ (5 mL) was added $Et_3N$ (3.20 mL, 22.5 mmol). The resulting solution was stirred at room temperature for 30 min. The solvent was removed in vacuo and the remaining oil was azeotroped with toluene (3×5 mL). The residue was dissolved in DMF (10 mL) and cooled to 0° C. Picolinic acid (2.80 g, 22.5 mmol), $Et_3N$ (3.20 mL, 22.5 mmol), EDC (4.70 g, 22.5 mmol) and HOBt (3.31 g, 22.5 mmol) were sequentially added. The reaction was allowed to warm to room temperature and maintained there for 18 h. The bulk of the solvent was removed in vacuo and the crude reaction mixture was partitioned between EtOAc (50 mL) and water (10 mL). The aqueous layer was acidified with 0.1N HCl (pH about 5). The organic layer was separated and dried over $MgSO_4$. Concentration afforded crude product which was recrystallized from $CHCl_3$/hexanes to give 3.20 g (66%) of the desired product.

b) (4S, 5R)-4-Carboxymethyl-4,5-dihydro-5-methyl-2-(2-pyridinyl)oxazole

To a solution of Pic-allo-ThrOMe (70.0 mg, 0.29 mmol, obtained as above) in THF (5 mL) was added in one portion (methoxycarbonylsulfamoyl)-triethylammonium hydroxide, inner salt (Burgess reagent) (80.0 mg, 0.34 mmol). When the Burgess reagent had dissolved, the reaction was heated to reflux for 18 h. After allowing the reaction to cool, the solvent was removed in vacuo. The crude reaction product was purified by flash chromatography (5% MeOH/EtOAc, silica gel) to give 40.0 mg (62%) of the desired product as a clear oil.

c) (4S, 5R)-4,5-Dihydro-5-methyl-2-(2-pyridinyl)oxazole-4-carboxylic acid

To a solution of (4S, 5R)-4-carboxymethyl-4,5-dihydro-5-methyl-2-(2-pyridinyl)oxazole (0.22 g, 1.00 mmol, obtained as above) in MeOH (2 mL) was added aq NaOH (44.0 mg, 1.10 mmol in 0.20 mL of $H_2O$ ). After 1 h at room temperature, the solvent was removed under reduced pressure. The residue was partitioned between EtOAc (5 mL) and 1N HCl (1 mL). The aqueous layer was extracted with further EtOAc (2×10 mL). the combined organic extracts were dried over $MgSO_4$ and concentrated to give a white residue. Flash chromatography (2% to 10% $MeOH/CHCl_3$+ 1% AcOH, silica gel) gave 80.0 mg (39%) of the desired compound as a white solid.

$^{13}C$ NMR (100 MHz, $CD_3OD$) d 181.9, 178.7, 165.8, 151.0, 146.5, 140.0, 128.4, 125.0, 84.0, 77.0.

MS (ES+) m/z 207.0 (M+H)

EXAMPLE 2

(4S, 5S)-4.5-Dihydro-5-methyl-2-(2-pyridinyl)oxazole4-carboxylic acid

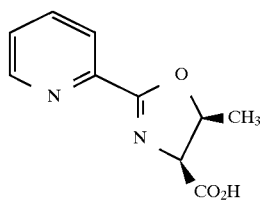

a) N-Picolinyl-threonyl methyl ester (Pic-ThrOMe)

In a fashion analogous to Example 1(a), ThrOMeoHCl (3.50 g, 20.4 mmol), $Et_3N$ (2×3.20 mL, 2×22.5 mmol), picolinic acid (2.80 g, 22.5 mmol), EDC (4.70 g, 22.5 mmol) and HOBt (3.31 g, 22.5 mmol) gave 3.45 g (71%) of the desired product after recrystallization from $CHCl_3$/hexanes.

b) (4S, 5S)4-Carboxymethyl4,5-dihydro-5-methyl-2-(2-pyridinyl)oxazole

In a fashion analogous to Example 1(b), Pic-ThrOMe (70.0 mg, 0.29 mmol), and Burgess reagent (80.0 mg, 0.34 mmol) gave 40.0 mg (62%) of the desired product as a clear oil.

c) (4S, 5R)-4,5-Dihydro-5-methyl-2-(2-pyridinyl)oxazole4-carboxylic acid

In a fashion analogous to Example 1(c), (4S, 5S)4-carboxymethyl-4,5-dihydro-5-methyl-2-(2-pyridinyl) oxazole (0.020 g, 0.09 mmol) and NaOH (4.0 mg, 0.10 mmol in 0.20 mL of $H_2O$) gave 8.0 mg (42%) of the desired compound as a white solid.

$^{13}C$ NMR (100 MHz, $CD_3OD$) d 181.9, 178.7, 165.8, 151.0, 146.5, 140.0, 128.4, 125.0, 84.0, 77.0.

MS (ES+) m/z 207.0 (M+H).

EXAMPLE 3

(4S, 5R)4,5-Dihydro-5-methyl-2-(2-pyridinyl)oxazole4-carboxamide

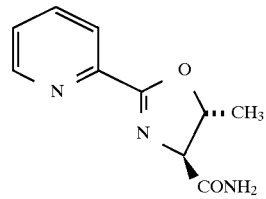

a) (4S, 5R)-4-Carboxymethyl-4,5-dihydro-5-methyl-2-(2-pyridinyl)oxazole (25 mg; 0.11 mmol obtained as in Example 1(b)) was dissolved in 2.0M $NH_3$ in MeOH (2 ml, 4.0 mmol). After 18 h at RT, the solvent was removed in vacuo. Purification using a Bond-Elut C18 column gave 4.9 mg (22%) of the desired product.

$^1H$ NMR (400 MHz, $CDCl_3$) d 8.7 (d; 1H); 8.1 (d, 1 H), 7.85 (m, 1 H), 7.45 (m,1 H), 6.8 (broad s;1H); 5.95 (broad s;1H); 5.1 (m, 1 H), 4.45 (d, 1 H), 1.65 (d, 3 H).

EXAMPLE 4

(4R, 5R)-4.5-Dihydro-5-methyl-2-(2-pyridinyl)oxazole-4-carboxylic acid

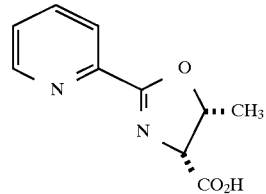

a) N-Picolinyl-d-threonyl methyl ester (Pic-d-ThrOMe)

In a fashion analogous to Example 1(a), d-ThrOMeOHCl (1.75 g, 10.2 mmol), $Et_3N$ (2×1.60 mL, 2×11.2 mmol), picolinic acid (1.40 g, 11.2 mmol), EDC (2.35 g, 11.2 mmol) and HOBt (1.16 g, 11.2 mmol) gave 1.95 g (73%) of the desired product after recrystallization from $CHCl_3$/hexanes.

b) (4R, 5R)-4-Carboxymethyl4,5-dihydro-5-methyl-2-(2-pyridinyl)oxazole

In a fashion analogous to Example 1(b), Pic-d-ThrOMe (0.35 g, 1.47 mmol) and Burgess reagent (0.50 g, 2.10 mmol) gave 0.20 g (63%) of the desired product as a clear oil.

c) (4R, 5R)4,5-Dihydro-5-methyl-2-(2-pyridinyl)oxazole4-carboxylic acid

In a fashion analogous to Example 1(c), (4R, 5R)-4-carboxymethyl-4,5-dihydro-5-methyl-2-(2-pyridinyl) oxazole (0.11 g, 0.50 mmol) and NaOH (22.0 mg, 0.55 mmol in 0.50 mL of $H_2O$) gave 8.0 mg (42%) of the desired compound as a white solid.

$^{13}C$ NMR (100 MHz, $CD_3OD$) d 181.9, 178.6, 166.2, 151.0, 146.5, 140.0, 128.4, 125.0, 84.4, 76.6.

MS (ES+) m/z 207.0 (M+H).

EXAMPLE 5

Formulations for pharmaceutical use incorporating compounds of the present invention can be prepared in various forms and with numerous excipients. Examples of such formulations are given below.

| Tablets/Ingredients | | |
|---|---|---|
| Per Tablet | | |
| 1. | Active ingredient (Cpd of Form. I) | 40 mg |
| 2. | Corn Starch | 20 mg |
| 3. | Alginic acid | 20 mg |
| 4. | Sodium alginate | 20 mg |
| 5. | Mg stearate | 1.3 mg |
| | | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its converion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

We claim:

1. A compound of Formula I:

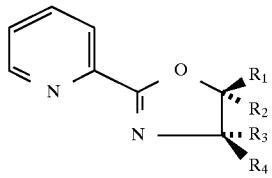

wherein:

$R_1$ and $R_2$ are independently hydrogen, $C_{1-6}$alkyl, phenyl, napthyl, benzyl,;

One of $R_3$ and $R_4$ is hydrogen and the other is —$CO_2H$, —$C(O)NH_2$, $C(O)C_{1-3}$alkyl, or $CSNH_2$,;

n is 1, 2 or 3;

provided at least one of $R_1$ and $R_2$ is not hydrogen;

or a pharmaceutically acceptable salt thereof.

2. A Compound of claim 1 selected from the group consisting of:

(4S,5R)-4,5-Dihydro-5-methyl-2-(2-pyridinyl)oxazole-4-carboxylic acid;

(4S,5S)-4,5-Dihydro-5-methyl-2-(2-pyridinyl)oxazole-4-carboxylic acid;

(4S,5R)-4,5-Dihydro-5-methyl-2-(2-pyridinyl)oxazole-4-carboxamide; and (4R,5R)-4,5-Dihydro-5-methyl-2-(2-pyridinyl)oxazole-4-carboxylic acid.

3. A pharmaceutical composition comprising an effective amount of a compound of claim 1 and a pharmaceutical acceptable carrier.

4. A method of providing a protective function in therapy using irradiation and or cytotoxic drugs and to arrest proliferation of cancer cells related to the myelopoietic system in an animal which comprises administering to a subject in need thereof, an effective amount of a compound of claim 1.

* * * * *